United States Patent [19]

Purdum

[11] 4,442,044
[45] Apr. 10, 1984

[54] PROCESS FOR PREPARING MONOESTERS AND DIESTERS OF N-ALKYL SUBSTITUTED AMINO METHYL PHOSPHONIC ACID

[75] Inventor: William R. Purdum, Maryland Heights, Mo.

[73] Assignee: Monsanto Company, St. Louis, Mo.

[21] Appl. No.: 479,246

[22] Filed: Mar. 28, 1983

Related U.S. Application Data

[63] Continuation-in-part of Ser. No. 275,487, Jun. 19, 1981, abandoned.

[51] Int. Cl.$^3$ ............................................... C07F 9/40
[52] U.S. Cl. .................................... 260/969; 260/941
[58] Field of Search .......................... 260/969, 502.5 F

[56] References Cited

FOREIGN PATENT DOCUMENTS 2005274  4/1979  United Kingdom .................... 71/86

Primary Examiner—Anton H. Sutto
Attorney, Agent, or Firm—David Bennett; Richard H. Shear; Arnold H. Cole

[57] ABSTRACT

A process for preparing monoesters and diesters of N-alkyl substituted amino methyl phosphonic acid which are useful as herbicides.

3 Claims, No Drawings

PROCESS FOR PREPARING MONOESTERS AND DIESTERS OF N-ALKYL SUBSTITUTED AMINO METHYL PHOSPHONIC ACID

This is a continuation in part of application Ser. No. 275,487 filed June 19, 1981 abandoned.

This invention relates to a process for preparing monoesters and diesters of N-alkyl substituted amino phosphonic acid which are useful as herbicides.

U.S. Pat. No. 4,025,331 issued to Jean-Pierre Leber on May 24, 1977 discloses N-phosphonomethylglycine derivatives of the formula

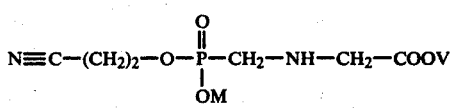

wherein V is hydrogen, unsubstituted or substituted hydrocarbon or a cation and O is hydrogen or a cation as well as a two reaction step process for preparing the same. The compounds disclosed in U.S. Pat. No. 4,025,331 supra are said to possess herbicidal and plant growth regulating properties.

U.S. Pat. No. 4,008,296 issued to John Edward Duncan Barton on Feb. 15, 1977 discloses a catalyzed process for preparing N-phosphonomethylglycine having the formula

which comprises (a) reacting 1,3,5-tricyanomethylhexahydro-1,3,4-triazine with an ester of phosphorous acid have the formula

wherein J and K are hydrocarbyl or substituted hydrocarbyl radicals, in the presence of a catalyst comprising a hydrogen halide, a Lewis acid, a carboxylic acid halide, or a carboxylic acid anhydride to form an ester of N-phosphonomethylgylcinonitrile, and (b) hydrolysing the ester of the N-phosphonomethylglycinonitrile: and recovering N-phosphonomethylglycine.

In accordance with the present invention monoesters and diesters of N-alkyl substituted amino methyl phosphonic acid of the formula

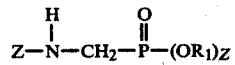

wherein Z is selected from the group consisting of

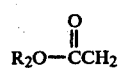

wherein $R_2$ is lower alkyl, lower alkoxy lower alkyl, halo lower alkyl, or phenyl lower alkyl;

lower alkynyl; lower alkyl or $N\equiv CCH_2$;

$R_1$ is selected from the group consisting of lower alkyl, lower alkoxy lower alkyl, halo lower alkyl, phenyl lower alkyl

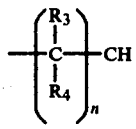

wherein n is an integer from 1 to 4, $R_3$ is selected from the group consisting of lower alkyl, lower alkoxy lower alkyl, halo lower alkyl, phenyl lower alkyl and $R_4$ is hydrogen or lower alkyl;

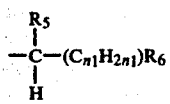

wherein $R_5$ is hydrogen, lower alkyl, lower alkoxy carbonyl; $R_6$ is halogen, lower alkoxy carbonyl or

wherein L is lower alkyl and $n_1$ is an integer from 0 to 3; $-(C_{n_2}H_{2n_2})S-X$ wherein X is lower alkyl or lower alkoxy carbonyl and $n_2$ is an integer from 1 to 4;

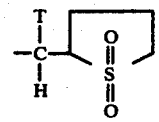

wherein T is lower alkyl; and $-(C_{n_3}H_{2n_3})-Y$, wherein $n_3$ is an integer from 0 to 4 and Y is selected from the group consisting of trihalomethyl, lower alkoxycarbonyl, furanyl, pyrolidinyl, pyranyl,

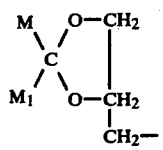

wherein $M_1$ and M are independently lower alkyl; may be prepared by simultaneously reacting a symmetrical tri-substituted phosphite of the formula $$P(OR_1)_3 \qquad (II)$$

wherein $R_1$ is defined as recited above with water and with 1,3,5-tri-substituted hexahydro-1,3,5-triazine (trimer of the Schiff's base of formaldehyde and a corresponding amine) of the formula

(III)

wherein Z is as aforedefined to form a crude diester or crude monoester composition containing diester and monoester product. A purified monoester or diester product may be recovered from the crude monoester or diester composition by employing a chromatographic and/or distillation means having sufficient capability and capacity to effect the aforedescribed recovery.

The aforedescribed reaction is carried out at a temperature in the range from about 10 to 110 and preferably from about 25° to about 100° C.

British patent application No. 2005 274 A which was published on Apr. 19, 1979 discloses a process in which a symmetrically-substituted triazine of the type described can be reacted with a sterically hindered diphosphite compound to produce a methylaminomethylphosphonate ester. It has however been found that reaction between a diester and the triazine, triester and water that is the subject of the present application. Additionally there is no requirement that the triester have any specific steric configuration.

The triester component of the reaction mixture can be obtained by reacting phophorous trichloride with three equivalents of the corresponding alcohol ($R_1OH$) in the presence of a base such as triethylamine in a suitable solvent. Such a process is described in "Organic Phosphorous Compounds" (Vol. 5) by G. M. Kosolapoff and L. Maier (Wiley-Interscience, 1973) at pp. 32—37.

The triazine components used in the above-described process are well known condensation products of formaldehyde with an amine having the formula $Z.NH_2$. Triazines of the type useful in the present invention are described for example, in "S-Triazines and Derivatives" by E. M. Smolin and L. Papoport, (Interscience 1959), pp. 480–3.

In preparing monoester and diester compounds of formula (I), the range of reactants is not narrowly critical. Preferably, however for each mole of tri-substituted phosphite employed, one should employ from about 0.5 to about 1.5 mole water, about ¼ to about 178 mole 1,3,5-tri-substituted hexahydro-1,3,5-triazine (which is equivalent to 1 mole of the monomer of a Schiff's base of formaldehyde and a corresponding amine.

As employed throughout the claims and description, the term "lower alkyl" includes alkyl radicals which have up to four carbon atoms in a straight or branched chain, for example, methyl, ethyl, propyl, isopropyl, butyl, isobutyl, sec-butyl and t-butyl.

As employed throughout the claims and description, the term "lower alkoxy" includes groups of the aforedescribed term "lower alkyl" which have one oxygen associated therewith such as methoxy, ethoxy, propoxy and butoxy.

Typical examples of the term "loweralkoxyloweralkyl" include groups representing combinations of the aforedefined term "lower alkyl" and the aforedefined term "lower-alkoxy" and include methoxymethyl, ethoxyethyl, propoxymethyl and the like.

The term "halo" includes chlorine, bromine, fluorine and iodine.

Illustrative groups of the term "phenylloweralkyl" are groups wherein the substituent on the phenyl comprising the aforedefined lower alkyl is in the ortho, meta, or para position, for example, phenylmethyl, phenylethyl, phenylpropyl, phenylbutyl, phenyl t-butyl and the like.

While no catalyst is required for the aforedescribed reaction to proceed, a catalyst may be employed if desired.

The reaction time is in the range from about 1 to about 72 and is preferably from about 2 to about 50 hours.

While the process of this invention can be conducted at atmospheric, sub-atmospheric or superatmospheric pressure, for convenience and economy it is generally preferred to conduct this process at atmospheric pressure.

Although a suitable solvent may be employed in the aforedescribed process, it is preferred that the reaction be carried out in the absence of a solvent.

Suitable agitation is provided, preferably by stirring or otherwise agitating the reaction composition.

In practicing the aforedescribed process the aforedescribed reactants are admixed together although the reactants may be admixed in any order desired to form a reaction composition.

The following examples are presented to define the invention more completely without any intention of being limited thereby. All parts and percentages are by weight, unless otherwise specified.

EXAMPLE 1

A reaction composition comprising 15.8 g (0.065 mole) tri-(1-cyanoethyl)phosphite, 1.2 g (0.065 mole) water, and 7.5 g (0.022 mole) 1,3,5-tri(ethoxycarbonymethyl)hexahydro-1,3,5-triazine was prepared and stirred while maintaining the reaction temperature at about 10° to about 20° C. with external cooling by an ice-water bath for a time of three hours. After completion of the reaction, α-hydroxypropionitrile a reaction alcohol coproduct was removed by employing bulb to bulb distillation at a pressure of 0.05 mm Hg and a temperature of 25° C. The desired glycine product was recovered by employing column chromatography of the distillation residue on cellulose (microcrystalline) with ethyl acetate:cyclohexane (1:3). The product, glycine, N-[[bis(1-cyanoethoxy)phosphinyl]methyl], ethyl ester, was obtained as a viscous reddish-colored oil at a yield of 2.0 grams (10.2%) and had the following analysis:

Calculated: C, 43.57; H, 5.98; N, 13.86; P, 10.21; Found: C, 44.09; H, 5.90; N, 14.67; P, 10.35.

EXAMPLE 2

A reaction composition comprising 15 g (0.053 mole) tri-(1-cyano-1-methylethyl)phosphite, 0.95 g (0.053 mole) water, and 6.11 g (0.0177 mole) 1,3,5-tri-(ethoxycarbonylmethyl)hexahydro-1,3,5-triazine was agitated at about 25° C. for 24 hours resulting in the formation of a pale-yellow-colored solution. The pale-yellow-colored solution was heated at about 50° C. for three hours with agitation. An alcohol coproduct α-hydroxyisobutyronitrile was left in solution. The reaction mixture was purified by employing chromatography on cellulose (microcrystalline) with the eluent ethyl acetate. The product, glycine, N-[bis(1-cyano-1-methylethoxy)phosphinylmethyl], ethyl ester, was obtained as a viscous reddish-brown oil having a yield of 16.6 g (94%) and had the following analysis:

Calculated: C, 47.13; H, 6.69; N, 12.68; P, 9.35; Found: C, 47.74; H, 6.72; N, 13.41; P, 9.10.

EXAMPLE 3

A mixture of 15.0 g (0.0622 mole) of tri-(1-cyanoethyl) phosphite, 1.12 g (0.0622 mole) of water and 4.17 g (0.0207 mole) of 1,3,5-tri-(propynyl)hexahydro-1,3,5-triazine was agitated at about 25° C. for six hours with a slight exotherm. An alcohol coproduct, 2-hydroxypropionitrile, was removed by bulb to bulb distillation at 25° C. and 0.1 mmHg. The distillation residue was chromatographed on microcrystalline cellulose with ethyl acetate as eluent. The compound, phosphonic acid, [(2-propnylamino)methyl]-,bis(1-cyanoethyl)ester was obtained as a viscous reddish-brown oil in a yield of 87% (13.8 g) and had the following analysis:

Calculated: C, 47.06; H, 5.53; N, 16.47; P, 12.14; Found: C, 47.16; H, 5.75; N, 16.09; P, 9.62;

Rechromatographed: Found: C, 47.19; H, 5.70; N, 16.10; P, 9.92.

EXAMPLE 4

A mixture of 15.0 g (0.0622 mole) of tri-(1-cyanoethyl) phosphite, 1.12 g (0.0622 mole) of water and 5.29 g (0.0207 mole) of 1,3,5-tri-(tertiary-butyl)-hexahydro-1,3,5-triazine was agitated at about 25° C. for six hours with a slight exotherm. An alcohol coproduct, 2-hydroxy-propionitrile, was removed by bulb to bulb distillation at 25° C. and 0.1 mmHg. The distillation residue was chromatographed on microcrystalline cellulose with ethyl acetate as eluent. The compound, (phosphonic acid, [[(1,1-dimethylethyl)amino]methyl]-,bis(1-cyanoethyl) ester) was obtained as a viscous orange oil in a yield of 82% (14.0 g) and had the following analysis:

Calculated: C, 48.35; H, 7.38; N, 15.38; P, 11.34; Found: C, 47.68; H, 7.09; N, 15.10; P, 9.32;

Rechromatographed: Found: C, 45.95; H, 7.15; N, 14.57; P, 10.68.

EXAMPLE 5

A reaction composition comprising 13.0 g (0.05 mole) tri-(1-cyanoethyl)phosphite, 0.97 g (0.05 mole) water, and 6.2 g (0.02 mole) 1,3,5-tri(ethoxycarbonylmethyl)-hexahydro-1,3,5-triazine was agitated at a temperature of about 25° C. for 5 hours. An alcohol co-product α-hydroxypropionitrile was removed by employing bulb to bulb distillation at 30° C. and 0.1 mmHg. The distillation residue was chromatographed on microcrystalline cellulose employing ethyl acetate as an eluent. A precipitate of the desired product, glycine, N-[[(1-cyanoethoxy)hydroxy-phosphinyl]methyl]ethyl ester, was formed in the effluent upon standing at about 25° C. for 12 hours. The yield was 0.5 g (4%). The analysis of the product was:

Calculated: C, 38.41; H, 6.04; N, 11.20; P, 12.38; Found: C, 38.35; H, 6.21; N, 11.25; P, 12.11.

EXAMPLE 6

A reaction composition comprising 10.5 g (0.04 mole) tri-(1-cyanoethyl)phosphite, 0.8 g (0.04 mole) water, and 6.8 g (0.01 mole) 1,3,5-tri(pentoxycarbonylmethyl)-hexahydro-1,3,5-triazine was agitated at a temperature of about 25° C. for 2 hours. An alcohol co-product α-hydroxypropionitrile was removed by employing bulb to bulb distillation at 50° C. and 0.1 mm Hg. The distillation residue was chromatographed on microcrystalline cellulose employing ethyl acetate/cyclohexane (⅓) as an eluent. A precipitate of the desired product, glycine, N-[[(1-cyanoethoxy)hydroxy-phosphinyl]methyl]pentyl ester, hemihydrate was formed in the effluent upon standing at about 25° C. for 12 hours. The yield was 2.0 g (16%). The analysis of said product was:

Calculated: C, 43.85; H, 7.36; N, 9.30; P, 10.28; Found: C, 43.50; H, 7.12; N, 9.57; P, 10.51.

EXAMPLE 7

A reaction composition comprising 11.5 g (0.05 mole) tri-(1-cyanoethyl)phosphite, 0.10 g (0.06 mole) water, and 7.3 g (0.02 mole) 1,3,5-tri(2-chloroethoxycarbonylmethyl)hexahydro-1,3,5-triazine was agitated at a temperature of about 25° C. for 16 hours. An alcohol co-product α-hydroxypropionitrile was removed by employing bulb to bulb distillation at 50° C. and 0.02 mm Hg. The distillation residue was chromatographed on microcrystalline cellulose employing ethyl acetate/cyclohexane (⅓) as an eluent. A solid precipitate of the desired product, glycine, N-[[(1-cyanoethoxy)hydroxyphosphinyl]methyl], 2-chloroethyl ester, was formed in the effluent upon standing at about 25° C. for 12 hours. The yield was 1.6 g (11%). The analysis of said product was:

Calculated: C, 33.76; H, 4.96; Cl, 12.46; N, 9.84; P, 10.88; Found: C, 33.87; H, 4.97; Cl, 12.27; N, 9.97; P, 11.05.

EXAMPLE 8

A reaction composition comprising 15.4 g (0.05 mole) tri-(1-cyanopropyl)phosphite, 0.9 g (0.05 mole) water, and 6.3 g (0.02 mole) 1,3,5-tri(ethoxycarbonylmethyl)-hexahydro-1,3,5-triazine was agitated at a temperature of about 25° C. for 12 hours. An alcohol co-product α-hydroxybutyronitrile was removed by employing bulb to bulb distillation at 25° C. and 0.05 mm Hg. The distillation residue was chromatographed on microcrystalline cellulose employing ethyl acetate/cyclohexane (⅓) as an eluent. A precipitate of the desired product, glycine, N-[[(1-cyanopropoxy)hydroxyphosphinyl]methyl],ethyl ester, was formed in the effluent upon standing at about 25° C. for 72 hours. The yield was 1 g (7%). The analysis of said product was:

Calculated: C, 40.91; H, 6.49; N, 10.60; P, 11.72; Found: C, 40.84; H, 6.67; N, 10.65; P, 11.71.

EXAMPLE 9

A reaction composition comprising 12.5 g (0.05 mole) tri-(1-cyanoethyl)phosphite, 0.9 g (0.05 mole) water, and 8.3 g (0.02 mole) 1,3,5-tri(2-ethoxyethoxycarbonylmethyl)hexahydro-1,3,5-triazine was agitated at a temperature of about 25° C. for 14 hours. An alcohol co-product α-hydroxypropionitrile was removed by employing bulb to bulb distillation at 55° C. and 0.1 mm Hg. The distillation residue was dissolved in ethyl acetate and agitated at about 25° C. for 72 hours with formation of the desired product, glycine, N-[[(1-cyanoethoxy)hydroxyphosphinyl]-methyl],2-ethoxyethyl ester as a precipitate.

The yield was 1.9 g (12%). The analysis of said product was:

Calculated: C, 40.82; H, 6.51; N, 9.52; P, 10.53; Found: C, 40.44; H, 6.62; N, 9.40; P, 10.30.

EXAMPLE 10

A reaction composition comprising 11.9 g (0.05 mole) tri-(1-cyanoethyl)phosphite, 0.9 g (0.05 mole) water, and 11.6 g (0.02 mole) 1,3,5-tri(phenylmethoxycarbonylmethyl)hexahydro-1,3,5-triazine was agitated at a temperature of about 25° C. for 48 hours. The reaction mixture was agitated with 100 ml ethyl acetate with formation of the desired product, glycine, N-[[(1-cyanoethoxy)hydroxyphosphinyl]methyl]-,phenylmethyl ester as a precipitate. The yield was 3.6 g (24%). The analysis of the product was:

Calculated: C, 50.00; H, 5.49; N, 8.97; P, 9.92; Found: C, 50.14; H, 5.49; N, 8.92; P, 9.87.

EXAMPLE 11

A reaction composition comprising 15.0 g (0.622 mole) tri-(2-cyanoethyl)phosphite, 1.12 g (0.0622 mole) water and 4.22 (0.0207 mole) of 1,3,5-tri(cyanomethyl)-hexahydro-1,3,5-triazine was agitated at about 25° C. for 12 hours. The resulting product composition was chromatographed on cellulose with ethyl acetate eluent. The product, phosphonic acid, [[(cyanomethyl)amino]-methyl],bis 2-(cyanoethyl)ester was isolated as a viscous reddish-brown oil having a yield of 7.2 g (45%) and the following analysis:

Calculated: C, 42.19; H, 5.11; N, 21.87; P, 12.07; Found: C, 42.89; H, 5.23; N, 21.20; P, 11.21.

EXAMPLE 12

A reaction composition comprising of 5 g (0.02 mole) tri-(1-cyanoethyl)phosphite, 0.37 g (0.02 mole) water and 1.4 g (0.0066 mole) of 1,3,5-tri(cyanomethyl)-hexahydro-1,3,5-triazine was agitated at about 15° C. for 16 hours. A α-hydroxypropionitrile co-product was removed by bulb to bulb distillation at 30° C. and 0.05 mm Hg. The distillation residue was chromatographed on cellulose (microcrystalline) with eluent of ethyl acetate:cyclohexane (1:3). The collected column concentrates were placed in vacuo at 60° C. (0.1 mmHg) for 30 minutes with the residue being the desired product. The product, phosphonic acid, [[(cyanomethyl)amino]-methyl],bis 1-cyanoethyl ester was obtained as a viscous reddish-colored oil having a yield of 1.4 g (27%) and the following analysis:

Calculated: C, 42.19; H, 5.11; N, 21.87; P, 12.09; Found: C, 42.14; H, 5.38; N, 20.45; P, 11.40.

EXAMPLE 13

A reaction composition comprising 15.0 g (0.0441 mole) tri(ethoxycarbonylmethyl)phosphite, 0.79 g (0.0441 mole) water and 5.08 g (0.0147 mole) 1,3,5-tri-(ethoxycarbonylmethyl) hexahydro-1,3,5-triazine was heated to about 100°–110° C. for three hours with agitation. An alcohol ethyl glycolate co-product was removed by bulb to bulb distillation of the reaction mixture at 75° C. and 0.1 mm Hg. The distillation residue was chromatographed on microcrystalline cellulose with an eluent of ethyl acetate. The product, glycine, N-[bis(ethoxycarbonylmethoxy)phosphinylmethyl]-, ethyl ester was obtained as a viscous yellow oil in 62% yield (10.1 g) having the following analysis:

Calculated: C, 42.28; H, 6.55; N, 3.79; P, 8.39; Found: C, 42.35; H, 6.12; N, 3.90; P, 8.54.

EXAMPLE 14

A reaction composition comprising 19.9 g (0.033 mole) tri(1,2-diethoxycarbonylethyl)phosphite, 0.6 g (0.033 mole) water and 3.8 g (0.011 mole) 1,3,5-tri-(ethoxycarbonylmethyl) hexahydro-1,3,5-triazine was heated to about 100°–110° C. for 2.5 hours with agitation. An alcohol diethyl malate (α-hydroxysuccinate) co-product was removed by bulb to bulb distillation of the reaction mixture at 75° C. and 0.1 mmHg. The distillation residue was chromatographed on silica gel with an eluent of ethyl acetate. The product, butanoic acid, 2,2'-[[[(2-ethoxy-2-oxo-ethyl)amino]methyl]phosphinylidene]bis(oxy)-bis-,tetraethyl ester was obtained as a viscous yellow oil in 13% yield (2.4 g) having the following analysis:

Calculated: C, 46.58; H, 6.70; N, 2.59; P, 5.72; Found: C, 46.75; H, 6.60; N, 2.85; P, 6.03.

EXAMPLE 15

A reaction composition comprising 15.0 g (0.0353 mole) butanoic acid, 3,3',3'',-phosphinidynetris(oxy)-tris-,triethyl ester, 0.64 g (0.0353 mole) water and 5.08 g (0.0147 mole) 1,3,5-tri-(ethoxycarbonylmethyl) hexahydro-1,3,5-triazine was heated to about 100°–110° C. for three hours with agitation. An alcohol co-product ethyl β-hydroxybutanoate was removed by bulb to bulb distillation of the reaction mixture at about 80° C. and 0.1 mmHg. The distillation residue was chromatographed on microcrystalline cellulose with an eluent of ethyl acetate. The product, butanoic acid, 3,3'-[[[[(2-ethoxy-2-oxoethyl]amino]methyl]phospinylidene]bis-(oxy)]bis-, diethyl ester was obtained as a viscous yellow oil in 61.3% yield (9.2 g) having the following analysis:

Calculated: C, 48.00; H, 7.58; N, 3.29; P, 7.28; Found: C, 47.03; H, 7.48; N, 3.56; P, 8.07.

EXAMPLE 16

A reaction composition comprising 15.0 g (0.039 mole) tri-(1-ethoxycarbonylethyl)phosphite, 0.71 g (0.039 mole) water and 4.525 g (0.0131 mole) 1,3,5-tri-(ethoxycarbonylmethyl)hexahydro-1,3,5-triazine was heated to about 100°–110° C. for three hours with agitation. An alcohol coproduct ethyl α-hydroxypropionate was removed by bulb to bulb distillation of the reaction mixture at 25° C. and 0.1 mmHg. The distillation residue was chromatographed on microcrystalline cellulose with an eluent of ethyl acetate. The product, propanoic acid, 2,2'-[[[[(2-ethoxy-2-oxoethyl)amino]methyl]phosphinylidene]bis(oxy)]-bis-, diethyl ester was obtained as a viscous yellow oil in 84.5% yield (13.1 g) having the following analysis:

Calculated: C, 45.34; H, 7.10; N, 3.53; P, 7.80; Found: C, 44.68; H, 6.69; N, 4.12; P, 8.56.

EXAMPLE 17

A reaction composition comprising 20.0 g (0.0742 mole) tri-(2-chloroethyl)phosphite, 1.34 g (0.0742 mole) water and 8.53 g (0.0247 mole) 1,3,5-tri-(ethoxycarbonylmethyl) hexahydro-1,3,5-triazine was heated to about 100°–110° C. for three hours with agitation. An alcohol 2-chloroethanol co-product was removed by bulb to bulb distillation of the reaction mixture at 25° C. and 0.1 mmHg. The distillation residue was chromatographed on microcrystalline cellulose with an eluent of ethyl acetate. The product, glycine, N-[[bis(2-chloroethoxy)phosphinyl]methyl]-, ethyl ester was obtained as a viscous yellow oil in 96.7% yield (23.1 g) having the following analysis:

Calculated: C, 33.56; H, 5.63; N, 4.35; P, 9.62; Found: C, 32.94; H, 5.65; N, 4.06; P, 9.51.

EXAMPLE 18

A reaction composition comprising 15.0 g (0.0441 mole) tri-(1-methoxycarbonylethyl)phosphite, 0.79 g (0.0441 mole) water and 5.08 g (0.0147 mole) 1,3,5-tri-(ethoxycarbonylmethyl)hexahydro-1,3,5-triazine was heated to about 100°–110° C. for three hours with agitation. An alcohol coproduct methyl α-hydroxypropionate co-product was removed by bulb to bulb distillation of the reaction mixture at 75° C. and 0.1 mmHg. The distillation residue was chromatographed on microcrystalline cellulose with an eluent of ethyl acetate. The product, propanoic acid, 2,2'-[[(ethoxycarbonylmethyl)amino]methylphosphinylidenedioxy]]bis-, dimethyl ester was obtained as a viscous yellow oil in 73.6% yield (9.2 g) having the following analysis:

Calculated: C, 42.28; H, 6.55; N, 3.79; P, 8.39; Found: C, 41.92; H, 6.23; N, 3.61; P, 7.74.

EXAMPLE 19

A reaction composition comprising 15.0 g (0.031 mole) tri-[[(2-ethoxycarbonyl)thio]ethyl]phosphite, 0.56 g (0.031 mole) water, and 3.59 g (0.0104 mole) 1,3,5-tri(ethoxycarbonylmethyl)hexahydro-1,3,5-triazine was heated at about 100° to about 110° C. for 3 hours with agitation. An alcohol 2-(ethoxycarbonylthio)ethanol co-product was removed by bulb to bulb distillation of the reaction mixture at 75° C. and 0.05 mmHg. The distillation residue was chromatographed on silica gel with ethyl acetate eluent. The product, glycine, N-[[bis[2-[(ethoxycarbonyl)thio]ethoxy]-phosphinyl]methyl]-, ethyl ester was obtained as a viscous yellow oil in 52% yield (7.4 g) having the following analysis:

Calculated: C, 39.04; H, 6.12; N, 3.04; P, 6.71; Found: C, 38.16; H, 6.16; N, 2.66; P, 6.20.

EXAMPLE 20

A reaction composition comprising 9.6 g (0.025 mole) tri-[tetrahydro-2H-thiopyran-3-yL]phosphite, 0.45 g (0.025 mole) water, and 2.9 g (0.008 mole) 1,3,5-tri(ethoxycarbonylmethyl)hexahydro-1,3,5-triazine was heated at about 100° to about 110° C. for 1½ hours with agitation. An alcohol tetrahydro-2H-thiopyran-3-ol co-product was removed by bulb to bulb distillation of the reaction mixture at 120° C. and 0.07 mmHg. The distillation residue was chromatographed on microcrystalline cellulose with an eluent of ethylacetate/cyclohexane (2:3). The product, glycine, N-[[bis[(tetrahydro-2H-thiopyran-3-yl)-oxy]-phosphinyl]methyl]-, ethyl ester was obtained as a viscous yellow oil in 40% yield (4.0 g) having the following analysis:

Calculated: C, 45.33; H, 7.10; N, 3.52; P, 7.79; S, 16.13; Found: C, 45.49; H, 7.28; N, 3.52; P, 7.60; S, 16.31.

EXAMPLE 21

A reaction composition comprising 15.0 g (0.045 mole) tri-(2-furanylmethyl)phosphite, 0.81 g (0.045 mole) water, and 5.18 g (0.015 mole) 1,3,5-tri(ethoxycarbonylmethyl)hexahydro-1,3,5-triazine was heated at about 100° to about 110° C. for a time of 3 hours. An alcohol --furanylmethanol coproduct was removed by employing bulb to bulb distillation of the reaction mixture at 75° C. and 0.05 mm Hg. The distillation residue was chromatographed on silica gel with an eluent of ethyl acetate. The product, glycine, N-[[bis(2-furanylmethoxy)phosphinyl]methyl]-, ethyl ester was obtained as a viscous yellow oil in 36.6% yield (6.0 g) having the following analysis:

Calculated: C, 49.31; H, 7.72; N, 3.83; P, 8.48; Found: C, 49.45; H, 8.33; N, 3.38; P, 7.56.

EXAMPLE 22

A reaction composition comprising 15.0 g (0.0353 mole) tri-[(2,2-dimethyl-1,3-dioxolan-4-yl)methyl]-phosphite, 0.64 g (0.0353 mole) water, and 4.07 g (0.0118 mole) 1,3,5-tri(ethoxycarbonylmethyl)hexahydro-1,3,5-triazine was heated at about 100° to about 110° C. for a time of 4 hours. An alcohol 2,2-dimethyl-1,3-dioxolan-4-yl methanol coproduct was removed by employing bulb to bulb distillation of the reaction mixture at 80° C. and 0.1 mm Hg. The distillation residue was chromatographed on silica gel with an eluent of ethyl acetate. The product, glycine, N-[[bis[(2,2-dimethyl-1,3-dioxolan-4-yl)methoxy]phosphinyl]methyl]-, ethyl ester was obtained as a viscous yellow oil in 35% yield (5.2 g) having the following analysis:

Calculated: C, 48.00; H, 7.58; N, 3.29; P, 7.28; Found: C, 48.57; H, 7.60; N, 2.74; P, 6.73.

EXAMPLE 23

A reaction composition comprising 15.0 g (0.04 mole) tri-[(tetrahydro-2H-pyran-2-yl]methyl)phosphite, 0.72 g (0.04 mole) water, and 4.6 g (0.0133 mole) 1,3,5-tri(ethoxycarbonylmethyl)hexahydro-1,3,5-triazine was heated at about 100° to about 110° C. for a time of 3 hours. An alcohol (tetrahydro-2H-pyran-2-yl)methanol byproduct was removed by employing bulb to bulb distillation of the reaction mixture at 75° C. and 0.1 mm Hg. The distillation residue was chromatographed on silica gel with an eluent of ethyl acetate. The product, glycine, N-[[bis(tetrahydro-2H-pyran-2-yl methoxy)-phosphinyl]methyl]-, ethyl ester was obtained as a viscous yellow oil in 57% yield (9.0 g) having the following analysis:

Calculated: C, 51.90; H, 8.20; N, 3.56; P, 7.87; Found: C, 51.86; H, 8.34; N, 3.37; P, 7.48.

EXAMPLE 24

A reaction composition comprising 15.0 g (0.0402 mole) tri-[2-(1-pyrrolidinyl)ethyl]phosphite, 0.72 g (0.0402 mole) water, and 4.63 g (0.0134 mole) 1,3,5-tri(ethoxycarbonylmethyl)hexahydro-1,3,5-triazine was heated at about 25° C. for 1 hour and then at about 100° to about 110° C. for 3 hours. The reaction mixture was chromatographed on microcrystalline cellulose with an eluent of ethyl acetate. The product, glycine, N-[[bis[2-(1-pyrrolidinyl)ethoxy]phosphinyl]methyl]-, ethyl ester was obtained as a viscous yellow oil in 41.3% yield (6.5 g) having the following analysis:

Calculated: C, 52.16; H, 8.75; N, 10.74; P, 7.91; Found: C, 52.62; H, 8.42; N, 10.85; P, 6.43.

EXAMPLE 25

A reaction composition comprising 15.0 g (0.0353 mole) butanoic acid, (3,3',3''-phosphinidyne tris(oxy)-tris-), triethyl ester, 0.64 g (0.0353 mole) water, and 4.08 g (0.0118 mole) 1,3,5-tri(ethoxycarbonylmethyl)hexahydro-1,3,5-triazine was heated at about 100° to about 110° C. for a time of 3 hours. An alcohol byproduct was removed by employing bulb to bulb distillation of the reaction mixture at about 80° C. and 0.1 mm Hg. The monoester product was obtained from a solution of ethyl acetate of the distillation residue upon standing at 25° C. for 48 hours. The product, butanoic acid, 3-

[[[[](2-ethoxy-2-oxoethyl)amino]methyl]-hydroxyphosphinyl]oxy]-, ethyl ester was obtained as a white solid in 8% yield (0.9 g) having a melting point of 116°–118° C. and having the following analysis:

Calculated: C, 42.44; H, 7.12; N, 4.50; P, 9.95; Found: C, 42.05; H, 7.11; N, 4.31; P, 9.98.

EXAMPLE 26

A reaction composition comprising 15.0 g (0.0315 mole) tri-(2,2,2-trichloroethyl)phosphite, 0.57 g (0.0315 mole) water, and 3.63 g (0.0105 mole) 1,3,5-tri(ethoxycarbonylmethyl)hexahydro-1,3,5-triazine was heated at about 100° to about 110° C. for a time of 3 hours. The reaction mixture was chromatographed on microcrystalline cellulose with an eluent of ethyl acetate. The product was precipitated from ethyl acetate eluent during 12 hours standing at 25° C. The product, glycine, N-[[(2,2,2-trichloroethoxy)hydroxyphosphinyl]methyl]-ethyl ester was obtained as a white solid in 14.7% yield (1.6 g) having a melting point of 143°–145° C. and having the following analysis:

Calculated: C, 24.26; H, 4.36; N, 4.04; P, 8.94; Found: C, 24.42; H, 3.48; N, 3.66; P, 7.87.

EXAMPLE 27

A reaction composition comprising 15.0 g (0.0315 mole) tri-(2,2,2trichloroethyl)phosphite, 0.57 g (0.0315 mole) water, and 3.63 g (0.0105 mole) 1,3,5-tri(ethoxycarbonylmethyl)hexahydro-1,3,5-triazine was heated at about 100° to about 110° C. for a time of 3 hours. The distillation residue was chromatographed on microcrystalline cellulose with an eluent of ethyl acetate. Upon standing for 12 hours at about 25° C. a hydrated form of the product precipitated. Upon standing the ethyl acetate filtrate after an additional 12 hours at 25° C. deposited the present product which was collected and dried at 40° C. and 0.1 mmHg over $P_2O_5$. The product, glycine, N-[[hydroxy(2,2,2-trichloroethoxy)-phosphinyl]methyl]-, ethyl ester was obtained as a white solid in 10.6% yield (1.1 g) having a melting point of 197°–199° C. and having the following analysis:

Calculated: C, 25.59; H, 3.99; N, 4.26; P, 9.43; Found: C, 25.85; H, 3.74; N, 4.44; P, 9.31.

If desired a diester compound of formula (I) may be hydrolyzed to a monoester compound of formula (I) by controlled hydrolysis. The temperature is in the range from about 15° to about 50° C. and is preferably from about 20° to about 30° C. Hydrolysis time is in the range from about 10 to about 60 and preferably from about 20 to about 40 minutes.

EXAMPLE 28

A reaction composition comprising 8.0 g (0.028 mole) of ethyl N[[bis 1-(1-methoxycarbonyl)ethoxy]phosphinyl]methylglycinate and 0.51 g (0.028 mole) water was agitated at about 25° C. for 30 minutes. The reaction mixture was chromatographed on a cation exchange column with water as eluent. The product, propanoic acid, 2-[[[[(2-ethoxy-2-oxoethyl)amino]methyl]-hydroxyphosphinyl]oxy]-, methyl ester was isolated as the fourth component determined by a refractive index detector in 41.6% yield (3.30 g) having the following analysis:

Calculated: C, 36.10; H, 6.67; N, 4.68; P, 10.34; Found: C, 36.18; H, 6.11; N, 4.56; P, 10.38.

EXAMPLE 29

The post-emergent herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergent herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A—Canada Thistle* | K—Barnyardgrass |
| B—Cocklebur | L—Soybean |
| C—Velvetleaf | M—Sugar Beet |
| D—Morningglory | N—Wheat |
| E—Lambsquarters | O—Rice |
| F—Smartweed | P—Sorghum |
| G—Yellow Nutsedge* | Q—Wild Buckwheat |
| H—Quackgrass* | R—Hemp Sesbania |
| I—Johnsongrass* | S—Panicum Spp |
| J—Downy Brome | T—Crabgrass |

*Established from vegetative propagules.

TABLE I

| Compound of Example No. | WAT | kg/h | A | B | C | D | E | F | G | H | I | J | K |
|---|---|---|---|---|---|---|---|---|---|---|---|---|---|
| 1 | 4 | 11.2 | 3 | 3 | 3 | 3 | 1 | 4 | 3 | 2 | 4 | 2 | 4 |
|  | 4 | 5.6 | 4 | 3 | 4 | 3 | 3 | 3 | 2 | 3 | 3 | 3 | 4 |
| 2 | 4 | 56.0 | 4 | 1 | 0 | 1 | 1 | 1 | 0 | 0 | 0 | 0 | 0 |
|  | 4 | 11.2 | — | 0 | 0 | 0 | 0 | 0 | 0 | 0 | 0 | 0 | 1 |
|  | 2 | 5.6 | — | 0 | 0 | 0 | 0 | 0 | 0 | 0 | 0 | 0 | 0 |
| 3 | 2 | 11.2 | 0 | 0 | 0 | 0 | 0 | 1 | 0 | 0 | 0 | 0 | 2 |
| 4 | 2 | 11.2 | 0 | 0 | 0 | 0 | 1 | 1 | 0 | 0 | 0 | 0 | 1 |
| 5 | 4 | 11.2 | 2 | 3 | 4 | 4 | 4 | 4 | 3 | 4 | 3 | 3 | 4 |
|  | 4 | 11.2 | 4 | 4 | 4 | 4 | 4 | 4 | 2 | 4 | 4 | 4 | 4 |
|  | 4 | 5.6 | 2 | 4 | 4 | 3 | 2 | 4 | 3 | 3 | 4 | 2 | 4 |
|  | 4 | 5.6 | 3 | 3 | 3 | 3 | 4 | 4 | 3 | 4 | 3 | 3 | 4 |
| 6 | 4 | 11.2 | 4 | 3 | 3 | 2 | 4 | 4 | 4 | 3 | 2 | 3 | 3 |
|  | 4 | 5.6 | 4 | 3 | 3 | 3 | 2 | 4 | 2 | 2 | 1 | 1 | 3 |
| 7 | 4 | 11.2 | 2 | 3 | 3 | 2 | 3 | 4 | 3 | 0 | 0 | 2 | 2 |
|  | 4 | 5.6 | 2 | 4 | 3 | 2 | 4 | 4 | — | 2 | 1 | 2 | 3 |
| 8 | 4 | 11.2 | 4 | 4 | 4 | 3 | 4 | 4 | 4 | 4 | 4 | 4 | 4 |
|  | 4 | 5.6 | 4 | 3 | 3 | 2 | 4 | 4 | 3 | 4 | 3 | 3 | 3 |
| 9 | 4 | 11.2 | — | 4 | 4 | 3 | 4 | 3 | 3 | 4 | 4 | 3 | 3 |
|  | 4 | 5.6 | — | 3 | 3 | 2 | 4 | 2 | 1 | 4 | 4 | 2 | 3 |
| 10 | 4 | 11.2 | 2 | 2 | 3 | 2 | 3 | 4 | 1 | 2 | 1 | 1 | 3 |
|  | 4 | 5.6 | 1 | 2 | 3 | 2 | 3 | — | 1 | 2 | 0 | 2 | 2 |
| 11 | 4 | 11.2 | 2 | 1 | 0 | 2 | 1 | 1 | 1 | 1 | 0 | 0 | 1 |
|  | 2 | 5.6 | 0 | 0 | 0 | 0 | 1 | 0 | 0 | 0 | 0 | 0 | 0 |
| 12 | 4 | 11.2 | 2 | 2 | 2 | 2 | 2 | 4 | 3 | 2 | 3 | 1 | 3 |
|  | 4 | 5.6 | 2 | 2 | 2 | 2 | 3 | 4 | 3 | 1 | 4 | 2 | 2 |
| 13 | 2 | 11.2 | 0 | 0 | 0 | 1 | 0 | 0 | 0 | 0 | 0 | 0 | 0 |
|  | 2 | 5.6 | 0 | 0 | 0 | 0 | — | 0 | 0 | 1 | 0 | 0 | 0 |
| 14 | 2 | 11.2 | 0 | 0 | 0 | 0 | 0 | 0 | 0 | 0 | 0 | 0 | 0 |
|  | 2 | 5.6 | 0 | 0 | 0 | 0 | 0 | 0 | 0 | 0 | 0 | 0 | 0 |
|  | 4 | 56.0 | 1 | 4 | 3 | 2 | 4 | 3 | 1 | 3 | 3 | 2 | 3 |
|  | 2 | 56.0 | 4 | 4 | 4 | 3 | 4 | 4 | 4 | 4 | 3 | 3 | 4 |
| 15 | 4 | 11.2 | 0 | 1 | 0 | 1 | 0 | 0 | 1 | 1 | 0 | 0 | 3 |
|  | 2 | 5.6 | 0 | 0 | 0 | 0 | 0 | 0 | 0 | 0 | 0 | 0 | 0 |
| 16 | 4 | 11.2 | 0 | 1 | 0 | 1 | 0 | 0 | 1 | 0 | 0 | 1 | 1 |
|  | 4 | 5.6 | 0 | 0 | 0 | 1 | 0 | 0 | 1 | 0 | 0 | 0 | 1 |
| 17 | 4 | 11.2 | 0 | 0 | 1 | 1 | 1 | 1 | 0 | 0 | 0 | 0 | 1 |
|  | 2 | 5.6 | 0 | 0 | 0 | 0 | 0 | 0 | 0 | 0 | 0 | 0 | 0 |
| 18 | 4 | 11.2 | 0 | 0 | 0 | 1 | 0 | 0 | 2 | 3 | 1 | 2 | 2 |
|  | 4 | 5.6 | 0 | 0 | 0 | 1 | 0 | 0 | 1 | 0 | 0 | 0 | 1 |
| 19 | 4 | 11.2 | 2 | 2 | 0 | 2 | 0 | 1 | 1 | 1 | 2 | 0 | 2 |
|  | 4 | 5.6 | 1 | 0 | 0 | 2 | 0 | 0 | 0 | 0 | 1 | 0 | 1 |
| 20 | 4 | 11.2 | 0 | 0 | 1 | 1 | 1 | 0 | 0 | 1 | 0 | 0 | 1 |
|  | 2 | 5.6 | 0 | 0 | 0 | 0 | 0 | 0 | 0 | 0 | 0 | 0 | 0 |
| 21 | 4 | 56.0 | 3 | 2 | 1 | 2 | 1 | 1 | 1 | 0 | 0 | 1 | 2 |
|  | 4 | 11.2 | 0 | 0 | 0 | 1 | 0 | 0 | 0 | 0 | 0 | 0 | 0 |
| 22 | 4 | 56.0 | 2 | 2 | 2 | 2 | 3 | 3 | 2 | 3 | 1 | 2 | 3 |
|  | 4 | 11.2 | 0 | 0 | 0 | 1 | 0 | 0 | 0 | 0 | 0 | 0 | 3 |
| 23 | 4 | 11.2 | 0 | 0 | 0 | 1 | 0 | 1 | 0 | 0 | — | 0 | 1 |
|  | 2 | 5.6 | 0 | 0 | 0 | 0 | 0 | 0 | 0 | 0 | 0 | 0 | 0 |
| 24 | 4 | 11.2 | 1 | 2 | 1 | 2 | 1 | 2 | 1 | 2 | 2 | 1 | 3 |
|  | 4 | 5.6 | 1 | 1 | 1 | 1 | 3 | 2 | 2 | 1 | 1 | 0 | 2 |
| 25 | 4 | 11.2 | 1 | 2 | 1 | 2 | 0 | 0 | 2 | 1 | 2 | 0 | 2 |
|  | 4 | 5.6 | 0 | 0 | 0 | 1 | 0 | 0 | 0 | 0 | 1 | 0 | 1 |
| 26 | 4 | 11.2 | 0 | 1 | 0 | 0 | 1 | 0 | 0 | 0 | 0 | 0 | 1 |
|  | 4 | 56.0 | 0 | 1 | 0 | 1 | 1 | 1 | 1 | 0 | 0 | 0 | 1 |
| 27 | 4 | 11.2 | 2 | 2 | 2 | 2 | 3 | 2 | 2 | 1 | 0 | 0 | 3 |
|  | 4 | 5.6 | 1 | 2 | 1 | 2 | 3 | 2 | 0 | 1 | 2 | 0 | 3 |
| 28 | 4 | 11.2 | 1 | 2 | 2 | 3 | 3 | 3 | 3 | 2 | 3 | 1 | 2 |
|  | 4 | 5.6 | 1 | 1 | 0 | 1 | 0 | 0 | 1 | 0 | 2 | 1 | 2 |

**Applied in 100 GPA THF immediately after formulation.
— Indicates species of plant absent during test.

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 4 | 4 | 4 | 4 | 4 | 3 | 4 | 3 | 2 | 3 | 4 | 4 | 4 | 4 | 4 | 4 |
|  | 4 | 1.12 | 2 | 4 | 2 | 1 | 3 | 2 | 2 | 2 | 5 | 3 | 3 | 2 | 2 | 4 | 3 | 3 |
|  | 4 | 0.28 | 0 | 2 | 1 | 0 | 1 | 1 | 0 | 1 | 0 | 0 | 0 | 0 | 2 | 2 | 1 |
| 5 | 4 | 5.6 | 4 | 4 | 4 | 4 | 4 | 4 | 4 | 3 | 4 | 4 | 3 | 4 | 4 | 4 |
|  | 4 | 1.12 | 2 | 2 | 3 | 2 | 3 | 2 | 2 | 2 | 2 | 4 | 4 | 2 | 2 | 4 | 3 | 4 |
|  | 4 | 0.28 | 1 | 1 | 1 | 0 | 3 | 2 | 0 | 2 | 1 | 2 | 2 | 1 | 1 | 3 | 3 | 3 |
| 6 | 4 | 5.6 | 4 | 4 | 4 | 4 | 4 | 3 | 4 | 3 | 4 | 4 | 3 | 3 | 4 | 4 | 3 | 4 |
|  | 4 | 1.12 | 2 | 4 | 2 | 2 | 3 | 2 | 2 | 2 | 2 | 3 | 3 | 2 | 3 | 4 | 3 | 3 |
|  | 4 | 0.28 | 1 | 2 | 2 | 1 | 1 | 2 | 2 | 2 | 1 | 1 | 1 | 1 | 3 | 4 | 2 | 3 |
| 7 | 4 | 5.6 | 3 | 4 | 4 | 3 | 3 | 3 | 2 | 2 | 4 | 2 | 4 | 3 | 3 | 3 | 3 | — |
|  | 4 | 1.12 | 2 | 3 | 3 | 3 | 2 | 2 | 2 | 2 | 2 | 3 | 2 | 2 | 4 | 3 | — |
|  | 4 | 0.28 | 1 | 4 | 3 | 1 | 2 | 2 | 2 | 1 | 3 | 4 | 4 | 2 | 2 | 3 | 2 | — |

TABLE II-continued

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| | 4 | 0.06 | 0 | 0 | 1 | 0 | 2 | 0 | 0 | 2 | 0 | 0 | 1 | 1 | 1 | 3 | 2 | 3 |
| | 2 | 0.01 | 0 | 0 | 0 | 0 | 0 | 0 | 0 | 1 | — | 1 | 0 | 0 | 0 | 0 | 0 | 2 |
| 8 | 4 | 5.6 | 4 | 4 | 4 | 4 | 4 | 4 | 4 | 3 | 4 | 4 | 4 | 3 | 3 | 4 | 4 | — |
| | 4 | 1.12 | 3 | 4 | 4 | 3 | 4 | 3 | 3 | 3 | 2 | 3 | 3 | 3 | 3 | 4 | 4 | — |
| | 2** | 0.056 | 0 | 0 | 1 | 0 | 0 | 0 | 0 | 0 | 0 | 0 | 0 | 0 | 0 | 0 | 1 | — |
| 9 | 4 | 5.6 | 4 | 4 | 3 | 3 | 3 | 4 | 3 | 2 | 1 | 4 | 1 | 3 | 4 | 4 | 3 | — |
| | 4 | 1.12 | 3 | 2 | 3 | 2 | 1 | 1 | 0 | 2 | 1 | 4 | 2 | 3 | 1 | 4 | 3 | — |
| | 4 | 0.28 | 1 | 3 | 2 | 1 | 2 | 1 | 1 | 2 | 1 | 4 | 2 | 1 | 2 | 4 | 2 | — |
| 10 | 4 | 5.6 | 3 | 3 | 2 | 2 | 3 | 3 | 3 | 2 | 1 | 3 | 4 | 1 | 2 | 4 | 3 | 4 |
| | 4 | 1.12 | 1 | 2 | 2 | 1 | 2 | 2 | 2 | 2 | 1 | 3 | 4 | 1 | 2 | 4 | 2 | 4 |
| | 4 | 0.28 | 1 | 3 | 1 | 0 | 2 | 1 | 1 | 2 | — | 2 | 4 | 1 | 1 | 3 | 2 | 4 |
| | 2 | 0.056 | 1 | 0 | 0 | 0 | 0 | 0 | 0 | 0 | 0 | 1 | 0 | 0 | 0 | 0 | 0 | 1 |
| | 2 | 0.011 | 0 | 0 | 0 | 0 | 0 | 0 | 0 | 0 | 0 | 0 | 0 | 0 | 0 | 0 | 0 | 0 |
| 12 | 4 | 5.6 | 1 | 1 | 2 | 2 | 4 | 3 | 0 | — | 0 | 4 | 2 | 2 | 3 | 1 | 3 | 2 |
| | 4 | 1.12 | 1 | 0 | 0 | 0 | 3 | 1 | 1 | 1 | 0 | 2 | 0 | 1 | 0 | 0 | 1 | 2 |
| | 2 | 0.28 | 0 | 0 | 0 | 0 | 1 | 0 | 0 | 0 | 0 | 1 | 0 | 0 | 0 | 0 | 0 | 0 |
| 13 | 2 | 5.6 | 1 | 0 | 2 | 0 | 1 | 1 | 0 | 1 | — | — | 1 | 1 | 0 | 0 | 1 | 3 |
| | 2 | 1.12 | 0 | 0 | 0 | 0 | 0 | 0 | 0 | 0 | 1 | 0 | 0 | 0 | 0 | 0 | 0 | 0 |
| | 2 | 0.28 | 0 | 0 | 0 | 0 | 0 | 0 | 0 | 0 | 0 | — | 0 | 0 | 0 | 0 | 0 | 0 |
| 15 | 4 | 5.6 | 1 | 0 | 1 | 0 | 0 | 0 | 0 | 1 | 0 | 1 | 0 | 0 | 0 | 1 | 0 | 2 |
| | 2 | 1.12 | 0 | 0 | 0 | 0 | 0 | 0 | 0 | 0 | 0 | 0 | 0 | 0 | 0 | 0 | 0 | 0 |
| 22 | 4 | 5.6 | 0 | 0 | 1 | 0 | 1 | 0 | 2 | 1 | — | 0 | — | 1 | 0 | 3 | 2 | 2 |
| | 2 | 1.12 | 0 | 0 | 0 | 0 | 0 | — | 0 | 0 | 2 | 1 | — | 0 | 0 | 0 | 1 | 1 |
| 24 | 4 | 5.6 | 2 | 1 | 2 | 2 | 2 | 3 | 1 | 2 | — | 3 | 2 | 2 | 2 | 4 | 3 | 4 |
| | 4 | 1.12 | 0 | 0 | 0 | 0 | 0 | 0 | 0 | 1 | 1 | 1 | 2 | 0 | 0 | 1 | 1 | 2 |
| 27 | 4 | 5.6 | 3 | 3 | 4 | 3 | 3 | 3 | 2 | 2 | 3 | 3 | 3 | 1 | 3 | 4 | 3 | 4 |
| | 4 | 1.12 | 2 | 2 | 2 | 3 | 2 | 2 | 2 | 2 | 2 | 2 | 2 | 1 | 3 | 4 | 3 | 3 |
| | 4 | 0.28 | 2 | 2 | 3 | 3 | 2 | 2 | 2 | 2 | 1 | 1 | 3 | 1 | 3 | 3 | 3 | — |
| | 2 | 0.06 | 0 | 0 | 0 | 0 | 0 | 0 | 0 | 0 | 0 | 0 | 0 | 0 | 0 | 0 | 0 | — |
| | 2 | 0.01 | 0 | 0 | 0 | 0 | 0 | 0 | 0 | 0 | 0 | 0 | 0 | 0 | 0 | 0 | 0 | — |
| 28 | 4 | 5.6 | 1 | 0 | 1 | 2 | 2 | 2 | 0 | 2 | 3 | 1 | 1 | 0 | 0 | 2 | 3 | 3 |
| | 2 | 1.12 | 1 | 0 | 0 | 0 | 0 | 0 | 0 | 1 | 0 | 0 | 0 | 0 | 0 | 0 | 1 | 2 |

— Species of plant absent during test.

EXAMPLE 30

The pre-emergent herbicidal activity of some of the compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III.

The pre-emergent herbicidal activity index used below is based upon average percent control of each species as follows:

| Percent Control | Index |
|---|---|
| 1–24% control | 0 |
| 25–49% control | 1 |
| 50–74% control | 2 |
| 75–100% control | 3 |

Plant species in the table are identified by the same code letters used in the previous example.

TABLE III

| Compound of Example No. | WAT | kg/h | A | B | C | D | E | F | G | H | I | J | K |
|---|---|---|---|---|---|---|---|---|---|---|---|---|---|
| 5 | 2 | 11.2 | 3 | 0 | 0 | 0 | 3 | 0 | 1 | 2 | 0 | 0 | 0 |
| 6 | 2 | 11.2 | 0 | 0 | 0 | 0 | 0 | 0 | 0 | 0 | 0 | 0 | 0 |
| 7 | 2 | 11.2 | 1 | 0 | 0 | 0 | 0 | 0 | 0 | 0 | 1 | 0 | 0 |
| 8 | 2 | 11.2 | 3 | 0 | 0 | 0 | 0 | 0 | 1 | 2 | 2 | 0 | 0 |
| 9 | 2 | 11.2 | — | 0 | 0 | 0 | 0 | 0 | 1 | 0 | 0 | 0 | 0 |
| 10 | 2 | 11.2 | 3 | 0 | 0 | 0 | 0 | 0 | 0 | 2 | 0 | 0 | 0 |

**Applied in 100 gallon per acre THF immediately after formulated.
— Indicates species of plant absent during test.

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another application method, shielded applicators may be employed to direct the liquid composition in the form of a spray onto the weeds while effectively shielding the crops from the spray.

These and other application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15-17, 1980; Auburn University Printing Service, Auburn, Ala. U.S.A., the teachings of which are incorporated herein by reference in their entirety.

Another method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

The aforementioned and other methods for applying liquid compositions to plants are discussed in detail in "Rope Wick Applicator—Tool With A Future", Dale, James E., pp. 3-4, "The Recirculating Sprayer and Roundup ® Herbicide," Derting, Claude W., pp. 5-7, and "C.D.A. Herbicide Application," McGarvey, Frank X., Weeds Today, Volume 11, Number 2, pp. 8-9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for the preparation of phosphonate compounds useful as herbicides of the formula

wherein Z is selected from the group consisting of

wherein $R_2$ is lower alkyl, lower alkoxy alkyl, halo lower alkyl or phenyl lower alkyl; lower alkynyl; lower alkyl; and $NCCH_2-$; and $R_1$ is selected from the group consisting of lower alkyl; lower alkoxy lower alkyl; halo lower alkyl; phenyl lower alkyl;

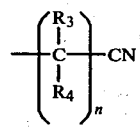

wherein n is an integer from 1 to 4, $R_3$ is selected from the group consisting of lower alkyl, lower alkoxy lower alkyl, halo lower alkyl, phenyl lower alkyl and $R_4$ is hydrogen or lower alkyl;

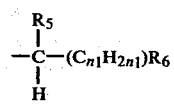

wherein $R_5$ is hydrogen, lower alkyl, lower alkoxy carbonyl; $R_6$ is halogen, lower alkoxy carbonyl, or

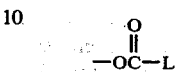

wherein L is lower alkyl and $n_1$ is an integer from 0 to 3; $(C_{n_2}H_{2n_2})S-X$ wherein X in lower alkyl or lower alkoxy carbonyl and $n_2$ is an integer from 1 to 4;

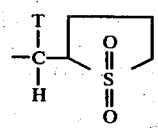

wherein T is lower alkyl; and $(C_{n_3}H_{2n_3})Y$ wherein $n_3$ is an integer from 0 to 4 and Y is selected from the group consisting of trihalomethyl, lower alkoxycarbonyl, furanyl, pyrrolidinyl, pyranyl and

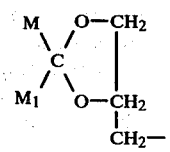

wherein $M_1$ and M are independently lower alkyl: said process comprising:
(a) reacting
 (i) a trisubstituted phosphite of the formula $P(OR_1)_3$ wherein $R_1$ is as defined above, with
 (ii) water, and
 (iii) a compound of the formula

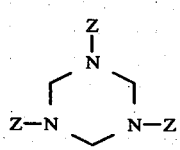

wherein Z is as aforedefined, to prepare a crude phosphonate composition containing said phosphonate compound, and
(b) thereafter recovering said phosphonate compound from said crude phosphonate composition.

2. The process according to claim 1 in which the reaction temperature is from about 10°-110° C.

3. The process according to claim 2 in which the reaction temperature is from about 20° to 100° C.

* * * * *

UNITED STATES PATENT AND TRADEMARK OFFICE
CERTIFICATE OF CORRECTION

PATENT NO. : 4,442,044

DATED : April 10, 1984

INVENTOR(S) : William R. Purdum

It is certified that error appears in the above-identified patent and that said Letters Patent is hereby corrected as shown below:

Column 1, line 39: "have" should be --having--.
Column 3, line 48: "178" should be --1/2--
Column 3, line 30: "phophorous" should be --phosphorous--
Column 9, line 40: "...thiopyran-3-yL ..." should be --...thiopyran-3-yl ...--

Column 9, line 63: "--furanylmethanol" should be --2-furanylmethanol--

Column 11, line 1: "[[[[]" should be --[[[[--

Columns 15-16, Table II-continued: between "Example No. 8, WAT 4 and Example No. 8, WAT 2**" insert

| WAT | kg/h | L | M | N | O | P | B | Q | D | R | E | F | C | J | S | K | T |
|-----|------|---|---|---|---|---|---|---|---|---|---|---|---|---|---|---|---|
| 4 | 0.28 | 1 | 1 | 2 | 0 | 2 | 2 | 1 | 2 | 1 | 1 | 1 | 0 | 2 | 3 | 3 | - |

Column 20, Claim 1, line 15: "in" should be --is--

Signed and Sealed this

Eleventh Day of September 1984

[SEAL]

Attest:

GERALD J. MOSSINGHOFF

Attesting Officer

Commissioner of Patents and Trademarks